(12) United States Patent
Zarroli et al.

(10) Patent No.: US 10,019,498 B2
(45) Date of Patent: Jul. 10, 2018

(54) BIOMETRIC DATA BROKERAGE SYSTEM AND METHOD FOR TRANSFER OF BIOMETRIC RECORDS BETWEEN BIOMETRIC COLLECTION DEVICES AND BIOMETRIC PROCESSING SERVICES

(71) Applicant: Northrop Grumman Systems Corporation, Falls Church, VA (US)

(72) Inventors: Gregory T. Zarroli, Midlothian, VA (US); Robert W. Johnston, Dawson, PA (US); Jay E. Orgeron, Yorktown, VA (US); Erik J. Bowman, Great Falls, VA (US); Taylor D. Baldwin, Newark, DE (US); Harry F. Richardson, Falls Church, VA (US); Kody West, Morgantown, WV (US)

(73) Assignee: NORTHRUP GRUMMAN SYSTEMS CORPORATION, Falls Church, VA (US)

( * ) Notice: Subject to any disclaimer, the term of this patent is extended or adjusted under 35 U.S.C. 154(b) by 25 days.

(21) Appl. No.: 14/675,058

(22) Filed: Mar. 31, 2015

(65) Prior Publication Data
US 2016/0294798 A1    Oct. 6, 2016

(51) Int. Cl.
G06F 7/04 (2006.01)
G06F 17/30 (2006.01)
H04L 29/06 (2006.01)

(52) U.S. Cl.
CPC .... G06F 17/30569 (2013.01); H04L 63/0861 (2013.01); H04L 63/0884 (2013.01)

(58) Field of Classification Search
CPC .......... G06F 21/32; G06F 21/10; G06F 21/31
See application file for complete search history.

(56) References Cited

U.S. PATENT DOCUMENTS

2002/0184538 A1* 12/2002 Sugimura ............... G06F 21/32
726/5
2007/0234066 A1* 10/2007 Dufour ............. G06F 17/30569
713/186

* cited by examiner

*Primary Examiner* — Catherine Thiaw
*Assistant Examiner* — Carlton Johnson
(74) *Attorney, Agent, or Firm* — Katten Muchin; Rosenman LLP

(57) ABSTRACT

A biometric data brokerage system (BDPS) and method for transfer of biometric records between at least one biometric collection device (BCD) and at least one biometric processing service (BPS) are disclosed. Embodiments provide a BDPS that utilizes biometric record translation routines that allow for biometric record submissions from any BCD to any BPS, regardless of biometric record format requirements. The need for costly and proprietary biometric record formatting software on BCDs is thereby eliminated.

25 Claims, 5 Drawing Sheets

BIOMETRIC DATA BROKERAGE SYSTEM AND METHOD FOR TRANSFER OF BIOMETRIC RECORDS BETWEEN BIOMETRIC COLLECTION DEVICES AND BIOMETRIC PROCESSING SERVICES

FIELD

Embodiments are in the technical field of biometric data systems, particularly biometric data brokerage systems. More particularly, embodiments disclosed herein relate to biometric data brokerage systems and methods for transfer of biometric records between biometric collection devices (BCDs) and biometric processing services (BPSs) which, inter alia, allows for biometric record submissions from any BCD to any backend matching service, regardless of biometric record format requirements, while eliminating the need for costly and proprietary biometric record formatting software on BCDs.

BACKGROUND

Current automated biometric identification systems consist of BCDs and BPSs. As a result, the system interface for these systems requires N-to-N connectivity, typically with custom, proprietary code, which is both expensive and insecure.

In order to provide biometric records to backend systems for processing (e.g., matching, enrollment, new hire onboarding, etc.), BCDs need to collect the biometrics, format all collected data into the appropriately formatted record, establish a connection with the backend system and transmit the record. If that record needs to be sent to multiple locations, the collection device user must individually initiate each transaction. Due to variations in the different formats, certain data points may need to be re-entered into different locations. The services which provide proper standards-based formatting are both expensive and proprietary. In addition, each BCD needs to have a custom connection component developed for each backend service to which it will need to connect, resulting in extensive throwaway development. Moreover, each connection must adhere to different security requirements which may overlap, differ, or even conflict with another connection's security requirements.

Today, a multitude of biometric hardware and software vendors provide proprietary biometric solutions for capture and matching of biometrics such as fingerprints, palm prints, iris, facial, and other measurable biological (anatomical or physiological) and behavioral characteristics that may be used for automated recognition. In many cases, the biometric devices meet some, but not all, of the various Department of Defense (DOD) and FBI standards for biometric capture and submission.

Thus, it is desirable to provide embodiments of a biometric data brokerage system and method for transfer of biometric records between BCDs and BPSs that are able to overcome the above disadvantages thereby eliminating, inter alia, the need for implementing costly, proprietary biometric record formatting software on capture devices.

SUMMARY

Embodiments are directed to a method for utilizing a BDPS to transfer biometric records between at least one BCD and at least one BPS. The method comprises: receiving, via a front-end BCD interface, biometric records in a first format transmitted by a first BCD, wherein the biometric records in the first format correspond to biometric data collected by the first BCD; translating, via an internal processes component, the biometric records in the first format received by the front-end BCD interface from the first format to a second format different from the first format; and transmitting, via a back-end BPS interface, the translated biometric records in the second format to a first BPS, wherein the translated biometric records in the second format is compatible with the first BPS.

In an embodiment, a method utilizes a BDPS to transfer biometric records between multiple BCDs and multiple BPSs.

In an embodiment, a method utilizes a BDPS to transfer biometric records in multiple formats between a BCD and multiple BPSs. In another embodiment, a method utilizes the BDPS to combine data corresponding to responses received from the multiple BPSs to form a single report, and for transmitting the single report to the BCD.

In an embodiment, the data corresponding to the response from the first BPS and the data corresponding to the response from the second BPS correspond to a single individual.

Embodiments are also directed to a system including a BDPS that transfers biometric records between at least one BCD and at least one BPS. The BDPS is placed between BCDs and BPSs. The BDPS includes three segments: a front-end BCD interface; an internal processes component; and a back-end BPS interface. The front-end BCD interface receives biometric records in a first format transmitted by a first BCD, wherein the biometric records in the first format correspond to biometric data collected by the first BCD. The internal processes component translates the biometric records in the first format received by the front-end BCD interface from the first format to a second format different from the first format. The back-end BPS interface transmits the translated biometric records in the second format to a first BPS, wherein the translated biometric records in the second format is compatible with the first BPS. Other system embodiments that have similarity to the various method embodiments are described below.

BRIEF DESCRIPTION OF THE DRAWINGS

The detailed description will refer to the following drawings in which like numerals refer to like items, and in which.

DETAILED DESCRIPTION

Figure 1:
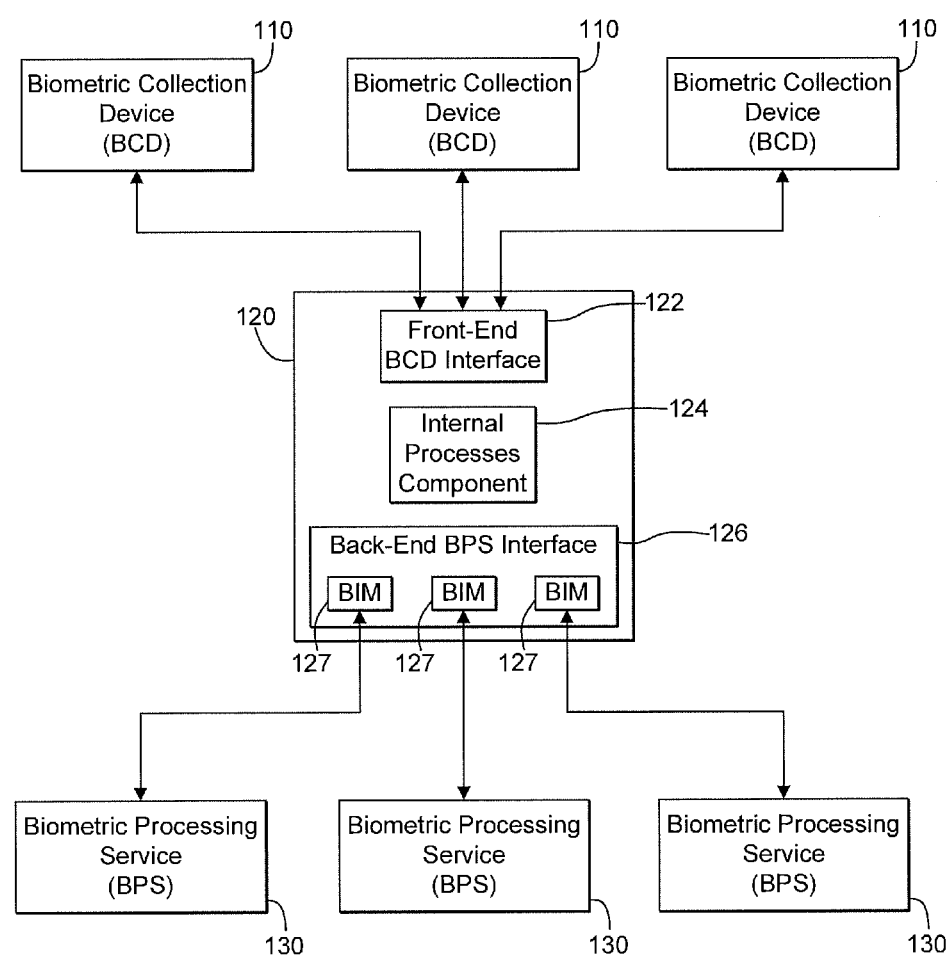
FIG. 1 is a block diagram of an embodiment of a system including a BDPS that transfers biometric records between at least one BCD and at least one BPS.

It is to be understood that the figures and descriptions of the present invention may have been simplified to illustrate elements that are relevant for a clear understanding of the present invention, while eliminating, for purposes of clarity, other elements found in a typical BCD or typical BPS, or typical method for transfer of biometric records from a BCD to a BPS. Those of ordinary skill in the art will recognize that other elements may be desirable and/or required in order to implement the present invention. However, because such elements are well known in the art, and because they do not facilitate a better understanding of the present invention, a discussion of such elements is not provided herein. It is also to be understood that the drawings included herewith only provide diagrammatic representations of the presently preferred structures of the present invention and that structures falling within the scope of the present invention may include structures different than those shown in the drawings. Reference will now be made to the drawings wherein like structures are provided with like reference designations.

Biometric data is a general phrase for computer data created during a biometric process. It includes, but is not limited to, raw sensor observations, biometric samples, models, templates and/or similarity scores. Biometric data is used to describe the information collected during an enrollment, verification, or identification process, but does not apply to end user information such as user name, demographic information, and authorizations.

Embodiments for utilizing a BDPS to transfer biometric records between at least one BCD and at least one BPS are described. The BDPS was conceived as a device agnostic biometric store and forward system that allowed biometric record submissions from any BCD to any backend matching service (or BPS), regardless of record format requirements. With the BDPS, the need for costly, proprietary biometric record formatting software on BCDs is eliminated.

The BDPS ingests biometric enrollment files of, for example, Extensible Markup Language (XML) type and translates those files into the appropriate standard(s) format necessary for processing by biometric processing repositories (or BPSs) such as Automated Biometric Identification System (ABIS), Integrated Automated Fingerprint Identification System (IAFIS), and/or Automated Biometric Identification System (IDENT), etc.

The BDPS facilitates the transfer of biometric records between BCDs and BPSs. The BDPS is a component designed to augment complex biometrically-enabled systems such as automated biometric identification systems for law enforcement and armed services or biometrically enabled enterprise systems (e.g. base access, HR management, etc.).

With reference to FIG. 1, shown is a block diagram of an embodiment of a system 100 including a BDPS 120 that transfers biometric records between at least one BCD 110 and at least one BPS 130. As the BDPS 120 is placed between BCDs 110 and BPSs 130, the BDPS 120 may be described as including three segments: a front-end BCD interface 122; an internal processes component 124; and a back-end BPS interface 126.

Front-End BCD Interface 122:

Critical to the BDPS 120 design, all BCDs 110 only need to interface with a single, unified interface, i.e., the front-end BCD interface 122. The front-end BCD interface 122 is considered "front-end" because the end users (i.e., via the BCDs 110) interact directly with this interface 122 which is the sole (or, at least, predominant) point of contact or connection of the BCDs 110 with the BDPS 120. All services are provided through a modern web services implementation that enables preferably both synchronous and asynchronous usage from any connected BCD (be it mobile, web-based, or legacy workstation applications). Since the BDPS 120 is designed to augment existing systems, the BDPS 120 also supports various legacy methods for submission including SMTP and SFTP transfers to ensure backwards compatibility with all currently used devices. In addition, all web services require the device to authenticate (e.g., through various mechanisms such as username/password, PKI, etc.) to the BDPS 120 before performing any tasks. This ensures that all users are authorized and provides a detailed audit trail of each task performed by each user.

Front-End BCD Interface 122 is meant to be a secure communication channel endpoint between BCDs 110 and BDPS 120. Physically, it is software component(s) running on BDPS 120 that expose secure ports for communication with BCDs 110. The Front-End BCD Interface 122 is unique in that it is designed to be flexible enough to understand and translate various payloads that are submitted over the secure interface.

In order to support multiple backend systems, which may each use different standards for biometric record formats, a data structure such as XML may be utilized that features all the details of the various formats in a more concise and more human-readable format. The XML format may preferably be reduced to its most concise form to best support mobile collection devices such as smart phones or tablets (or stand alone biometric collection devices) that use lower bandwidth connections than traditionally used. In addition, the XML format is designed to be highly configurable so as to allow many customized requirements to be defined (even while the user is in the field). By enabling heavily customizable mission requirements, the user can be explicitly directed as to what and how many biometrics need to be captured to be considered complete. In another step to support legacy devices, the web services can also accept records of various standards.

Internal Processes Component 124:

More than just a store and forward service, BDPS 120 has several components to ensure intelligent behavior and timely results. As the BDPS 120 can ingest biometric records in either a defined XML format or in any biometric record standard, the BDPS 120 needs to be able to translate from XML to a standard, from a standard to XML, or from one standard to another. In order to accomplish this task, the Internal Processes Component 124 includes a Biometric Record Translation Engine (BRTE) that utilizes data modeling and feature mapping rules distilled from, for example, the DOD, FBI, and/or National Institute of Standards and Technology (NIST) standards, as well as from rules derived from biometric processing systems operation. While ingested records can simply be translated and sent out, BPS 130 responses must be fused into a single response to provide concise, meaningful data back to the users. Data from disparate BPS 130 responses are combined into a single report. Records from multiple systems which represent the same individual are combined into a single entity. Reports will also include any BPS 130 status details relevant to the user (e.g., service unavailable).

The BDPS 120 may therefore use an XML structure that merges NIST, FBI, and the DOD standards into a lightweight payload without reducing capability. By using data modeling, data translation, and similar heuristics, the BDPS 120 is able to map the XML format to multiple standards, variations, and versions. Then significant changes to these standards result in new mapping within the BDPS 120 while maintaining legacy support. The BDPS 120 is able to execute advanced validation closer to agents to ensure errors are quickly corrected without the need to validate against enterprise biometric matching services.

In order to ensure that each ingested request is fully processed, the BDPS 120 contains a Biometric Record Processing Manager (BRPM) which is responsible for all the tasks associated with each record. Once a record is received from the web services interface, the BRPM analyzes the user's credentials and affiliations, the type of record submitted, the BCD 110 from which the record originated, and any explicitly defined instructions to determine where the record needs to be processed and to where/whom the results need to be disseminated. The BRPM handles status updates and responses from the back-end BPS interface 126 to handle resubmissions, processing errors, and response on the user's behalf to ensure timely responses.

Back-End BPS Interface 126:

the BDPS 120 is designed such that once integrated with a biometric system, the BDPS 120 is the sole (or, at least, predominant) liaison with a BPS 130. The back-end BCD interface 126 is considered "back-end" because the end users (i.e., via the BCDs 110) do not interact directly with this interface 126 which is the sole (or, at least, predominant) point of contact or connection of the BPSs 130 with the BDPS 120. Given the heterogeneity of each BPS 130, the BDPS 120 has a custom biometric interface module (BIM) 127 for each BPS 130. These BIMs 127 handle the connection establishment, data transfers, and response acquisitions according to all requirements defined by the specific BPS 130. Each BIM 127 handles the security and credential management needed to establish a connection with its BPS 130 including additional audit requirements and authentication mechanisms. Since the BDPS 120 resides on a powerful web server (in contrast to a smart-phone BCD), a vigorous encryption mechanism (e.g. a two-tiered VPN tunnel) may be deployed without draining constrained resources. Since each BPS 130 may feature a different response acquisition mechanism (e.g., SMTP, polling, SFTP delivery, etc.), each BIM 127 provides that mechanism to abstract the variations from the BRPM to ensure seamless behavior.

Back-End BPS Interface 126 is similar to Front-End BCD Interface 122. Back-End BPS Interface 126 is meant to be first a client for submitting a message payload over the interface exposed by BPS 130. Back-End BPS Interface 126 is designed to also receive the response ultimately generated by BPS 130. Physically, it is software component(s) running on BDPS 120 and it is designed to be flexibility enough to be able to communicate with various BPSs 130 and their sometimes complicated payloads.

The BDPS 120 allows biometric collections to be "fire-and-forget," so that an agent may perform multiple biometric captures via a BCD 110, submit the records, and continue his/her necessary duties. If the match results of the submissions provide identification from a specific system, or the results of fusion within the BDPS 120, then the BDPS 120 will retrieve the relevant data from the BPS(s) 130 and provide the meaningful information that enables the agent/warfighter to make an intelligent decision. Also, due to the data translation engine, the results from differing systems can be fused into a single response that is provided to the agent via the BCD 110. Consequently, the agent may only be interrupted when he/she receives an actionable response.

As mentioned in the Background section above, current automated biometric identification systems consist of BCDs and BPSs. As a result, the current system interface requires N-to-N connectivity, typically with custom, proprietary code, which is both expensive and insecure. By inserting the BDPS 120 between the BCDs 110 and the BPSs 130, the complexity is drastically reduced as all BCDs 110 only need to communicate with one service (i.e., the BDPS 120) and, in turn, that service handles connectivity to all backend services (i.e., BPSs 130). By reducing the number of connections on the BCDs 110 to one, the BCDs 110 only need to maintain a single connection and only need to provide a single format, thus eliminating the need for expensive, proprietary standards formatting services on each BCD 110. Since the BCDs 110 have a single point of contact to all BPSs 130, each BCD 110 user may submit appropriate records to multiple, heterogeneous backend services through a single submission which drastically reduces a user's workload as compared to the user submitting each record individually as with current biometric identification systems. As a result of the reduced complexity, critical biometric transmission and verification may be provided in near real time, and both integration and maintenance costs are driven down.

Rather than ensuring that each BCD 110 has the capability to communicate with each BPS 130, the BDPS 120 provides a uniform interface that allows BCDs 110 to draw information from a variety of BPSs 130 simultaneously, i.e., via the BDPS 120. As a web services capability, the BDPS 120 drastically reduces the attack space exposed allowing for a clearly defined perimeter. Consequently, BCDs 110 only need to support the security and authentication mechanisms to connect with the BDPS 120. The BDPS 120 then handles connections to the disparate service providers (BPSs 130) through a secure tunnel which offers a significantly cleaner audit capability. In addition, BCDs 110 with low bandwidth send the data to the BDPS 120 which allows the higher bandwidth of the BDPS 120 to send multiple records out to various BPSs 130.

Since cyber security is a topic of great national interest, any means to reduce susceptibility to attack can be advantageous. With each BCD needing connectivity to each backend system, the current automated biometric identification systems presented extensive attack spaces and required overly complex audit tracking. With the BDPS 120, BCDs 110 no longer need to be on the same, typically highly secure, networks as the backend services. Instead, the BDPS 120 acts as a portal on the edge of the secure network and all secure connections are securely routed from a single point. This reduction in communications means the BDPS 120 can provide an accurate, easy to track audit log of connections from BCDs 110 and each BPS 130 will only contain audit logs with the the BDPS 120. This reduction in communications also provides a very limited attack space in that the BDPS 120 (and not every single BCD 110) is the only means of entry into the secure network. Thus, very stringent and redundant security mechanisms can be layered at this entrance present by the BDPS 120 rather than deploying the same mechanisms to every BCD 110 and BPS 130.

Figure 2:
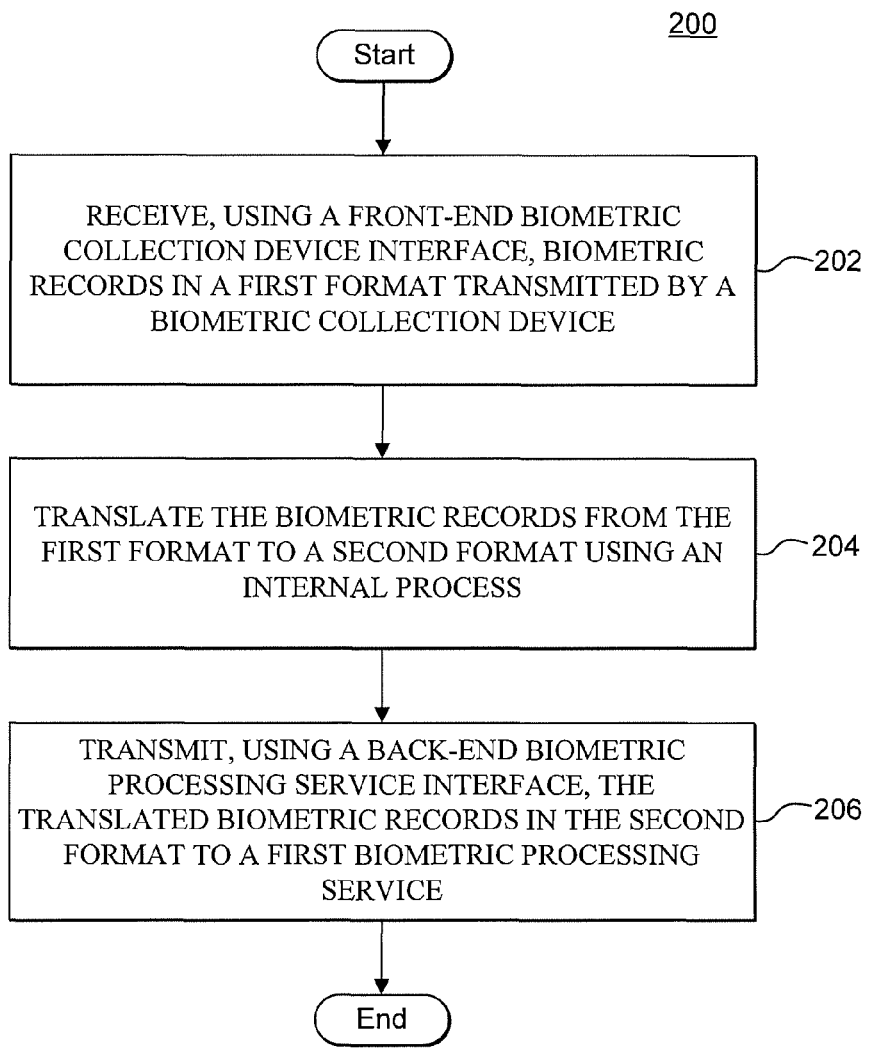
FIG. 2 is a flowchart illustrating an embodiment of a method for utilizing a BDPS to transfer biometric records between at least one BCD and at least one BPS.

With reference to FIG. 2, shown is a flowchart illustrating an embodiment of a method 200 for utilizing a BDPS to transfer biometric records between at least one BCD and at least one BPS. The method 200 comprises: receiving, via using a front-end BCD interface, biometric records in a first format transmitted by a first BCD (block 202), wherein the biometric records in the first format correspond to biometric data collected by the first BCD; translating, using an internal process (i.e., via an internal processes component such as internal processes component 124 (see FIG. 1) which per-forms processes internal of the BDPS 120), the biometric records in the first format received by the front-end BCD interface from the first format to a second format (block 204), wherein the second format is different from the first format; and transmitting, via using a back-end BPS interface, the translated biometric records in the second format to a first BPS (block 206), wherein the translated biometric records in the second format is compatible with the first BPS. With the translation performed (i.e., via internal processes component 124), of the biometric records from a first format to a second format as per block 204, the BCDs 110 only need to maintain a single connection with front-end BCD interface 122. Regardless of the format compatible with the BPSs 130, the biometric records transmitted by each BCD (which can be in the same format for all BCDs or in formats which are different for each BCD) do not need to be translated by the BCDs and thus can be transmitted by the BCDs in any format since the translation of the biometric records into a format compatible with the targeted BPS is performed via the internal processes component 124 within the BDPS 120. Since the BCDs 110 have a single point of contact to all BPSs 130 (i.e., via the BDPS 120), each BCD 110 user may submit appropriate records to multiple, heterogeneous BPSs 130 through a single submission.

The translation that occurs within BDPS 120 is flexible and extensible and can change as new message payloads are added in the future. The BDPS 120 will ingest the inbound message from BCD 110 and based on the content of that message and the final destination(s) of the ultimate search request, be able to map the fields from the inbound message to a completely different outbound message payload. In non-technical terms, think of it as asking a global question in English and having a translator be able to ask the same question in many different other languages to other countries, then understanding the answers from those other countries, and ultimately consolidating all of the responses and responding in English back to the originator of the question. Thus, the burden is removed from any submitter (BCD 110) from knowing: a) how to communicate with any backend BPS 130; or b) where any backend BPS 130 physically resides.

Figure 3:
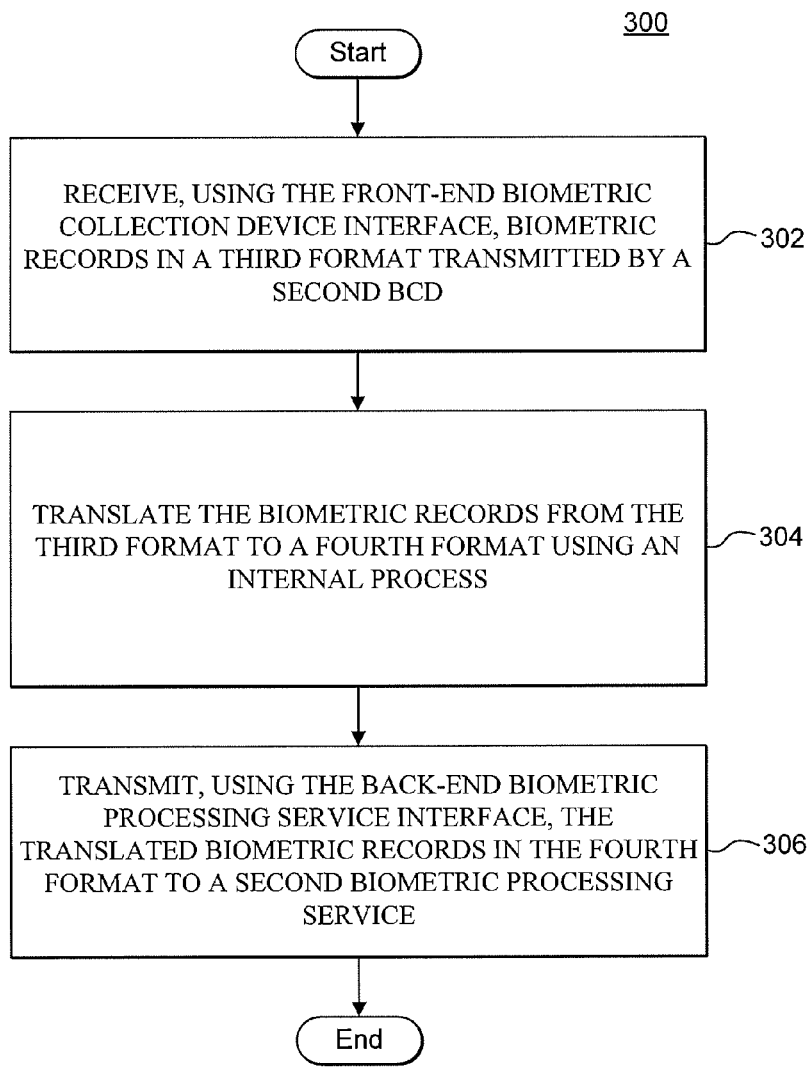
FIG. 3 is a flowchart illustrating an embodiment of a method for utilizing a BDPS to transfer biometric records between multiple BCDs and multiple BPSs.

With reference to FIG. 3, shown is a flowchart illustrating an embodiment of a method 300 for utilizing a BDPS to transfer biometric records between multiple BCDs and multiple BPSs. The method 300 builds on method 200 and further comprises: receiving, via using the front-end BCD interface, biometric records in a third format transmitted by a second BCD (block 302), wherein the biometric records in the third format correspond to biometric data collected by the second BCD; translating, using an internal process (i.e., via the internal processes component), the biometric records in the third format received by the front-end BCD interface from the third format to a fourth format (block 304), wherein the third format is different from the first and second formats, and the fourth format is different from the first, second, and third formats; and transmitting, via using the back-end BPS interface, the translated biometric records in the fourth format to a second BPS (block 306), wherein the translated biometric records in the fourth format is compatible with the second BPS.

Figure 4:
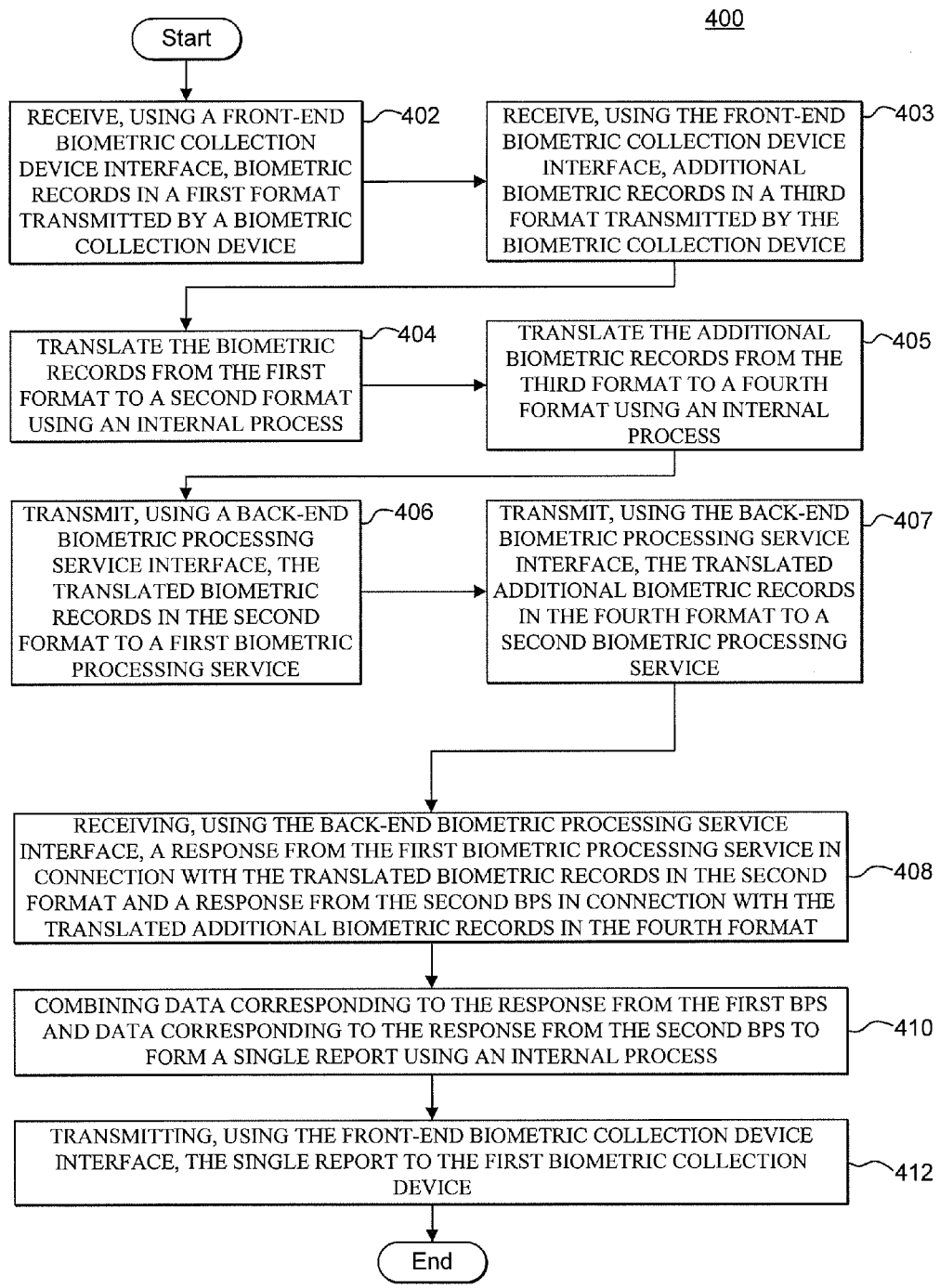
FIG. 4 is a flowchart illustrating an embodiment of a method for utilizing a BDPS to transfer biometric records in multiple formats between a BCD and multiple BPSs. The flowchart also illustrates an embodiment of a method for utilizing the BDPS to combine data corresponding to responses received from the multiple BPSs to form a single report, and for transmitting the single report to the BCD.

With reference to FIG. 4, shown is a flowchart illustrating an embodiment of a method 400 for utilizing a BDPS to transfer biometric records in multiple formats between a BCD and multiple BPSs. The flowchart also illustrates an embodiment of a method for utilizing the BDPS to combine data corresponding to responses received from the multiple BPSs to form a single report, and for transmitting the single report to the BCD. The method 400 includes blocks 402, 404, and 406 which correspond to blocks 202, 204, and 206, respectively, from method 200 in FIG. 2. However, method 400 in FIG. 4 builds on method 200 wherein the receiving further comprises receiving, via using the front-end BCD interface, additional biometric records in a third format transmitted by the first BCD (block 403), and wherein the additional biometric records in the third format correspond to additional biometric data collected by the first BCD; wherein the translating further comprises translating, using an internal process (i.e., via the internal processes component), the additional biometric records in the third format received by the front-end BCD interface from the third format to a fourth format (block 405), and wherein the third format is different from the first and second formats, and the fourth format is different from the first, second, and third formats; and wherein the transmitting further comprises transmitting, via using the back-end BPS interface, the translated additional biometric records in the fourth format to a second BPS (block 407), and wherein the translated additional biometric records in the fourth format is compatible with the second BPS.

The method 400 may further comprise: receiving, via using the back-end BPS interface, a response from the first BPS in connection with the translated biometric records in the second format and a response from the second BPS in connection with the translated additional biometric records in the fourth format (block 408); combining, using an internal process (i.e., via the internal processes component), data corresponding to the response from the first BPS and data corresponding to the response from the second BPS to form a single report (block 410); and transmitting, via using the front-end BCD interface, the single report to the first BCD (block 412).

In an embodiment, the data corresponding to the response from the first BPS and the data corresponding to the response from the second BPS correspond to a single individual.

Figure 5:
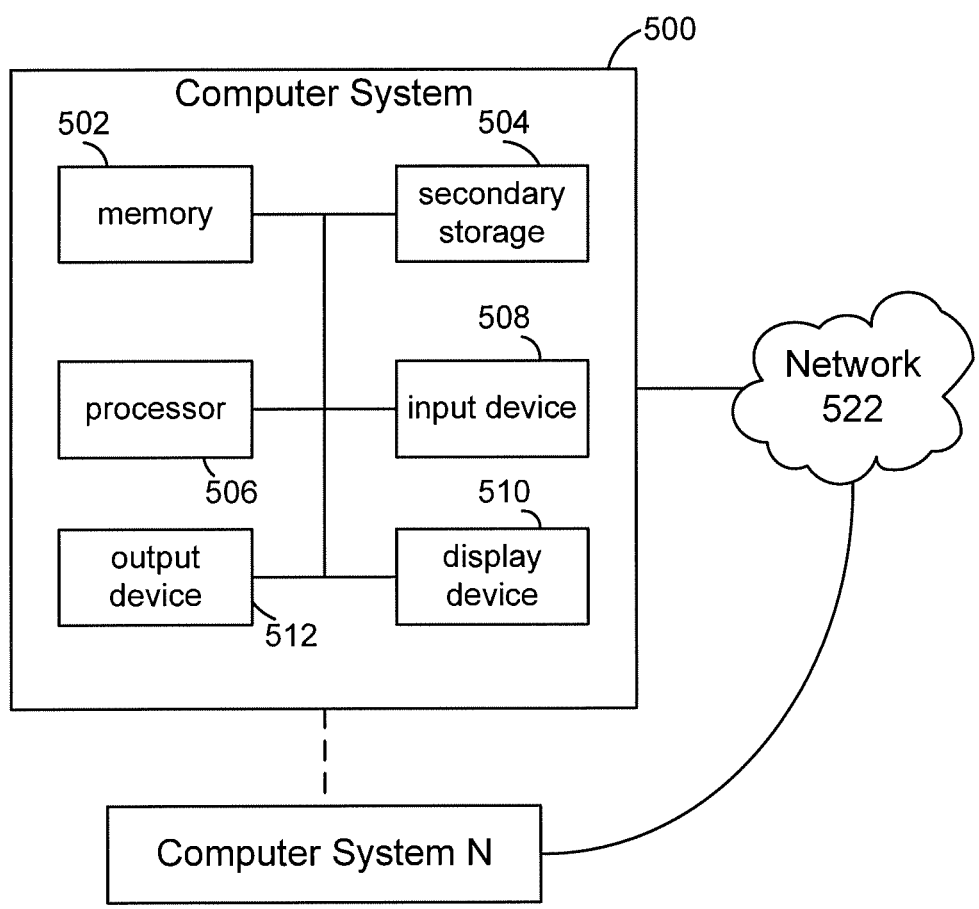
FIG. 5 is a block diagram illustrating an embodiment of a computer system that may be used in embodiments of a system including a BDPS that transfers biometric records between a BCD and a BPS.

With reference to FIG. 5, shown is a block diagram illustrating exemplary hardware components for implementing embodiments of a system including a BDPS that transfers biometric records between at least one BCD and at least one BPS, and a method thereof. Computer system 500, including client-servers combining multiple computer systems, or other computer systems similarly configured, may include and execute one or more subsystem components to perform functions described herein, including steps of methods and processes described above. Computer system 500 may connect with network 522, e.g., Internet, or other network, to receive inquires, obtain data, and transmit information and incentives as described above.

Computer system 500 typically includes a memory 502, a secondary storage device 504, and a processor 506. Computer system 500 may also include a plurality of processors 506 and be configured as a plurality of, e.g., bladed servers, or other known server configurations. Computer system 500 may also include an input device 508, a display device 510, and an output device 512. Memory 502 may include RAM or similar types of memory, and it may store one or more applications for execution by processor 506. Secondary storage device 504 may include a hard disk drive, floppy disk drive, CD-ROM drive, or other types of non-volatile data storage. Processor 506 executes the application(s), such as subsystem components, which are stored in memory 502 or secondary storage 504 or received from the Internet or other network 522. The processing by processor 506 may be implemented in software, such as software modules, for execution by computers or other machines. These applications preferably include instructions executable to perform the system and subsystem component (or application) functions and methods described above and illustrated in the FIGS. herein. The applications preferably provide graphical user interfaces (GUIs) through which users may view and interact with subsystem components (or application in mobile device).

Computer system 500 may store one or more database structures in secondary storage 504, for example, for storing and maintaining databases, and other information necessary to perform the above-described methods. Alternatively, such databases may be in storage devices separate from subsystem components.

Also, as noted, processor 506 may execute one or more software applications in order to provide the functions described in this specification, specifically to execute and perform the steps and functions in the methods described above. Such methods and the processing may be implemented in software, such as software modules, for execution by computers or other machines. The GUIs may be formatted, for example, as web pages in HyperText Markup Language (HTML), Extensible Markup Language (XML) or in any other suitable form for presentation on a display device depending upon applications used by users to interact with the system (or application).

Input device 508 may include any device for entering information into computer system 500, such as a touchscreen, keyboard, mouse, cursor-control device, touchscreen, microphone, digital camera, video recorder or camcorder. The input device 508 may be used to enter information into GUIs during performance of the methods described above. Display device 510 may include any type of device for presenting visual information such as, for example, a computer monitor or flat-screen display (or mobile device screen). The display device 510 may display the GUIs and/or output from sub-system components (or application). Output device 512 may include any type of device for presenting a hard copy of information, such as a printer, and other types of output devices include speakers or any device for providing information in audio form.

Examples of computer system 500 include dedicated server computers, such as bladed servers, personal computers, laptop computers, notebook computers, palm top computers, network computers, mobile devices, or any processor-controlled device capable of executing a web browser or other type of application for interacting with the system.

Although only one computer system 500 is shown in detail, system and method embodiments described herein may use multiple computer system or servers as necessary or desired to support the users and may also use back-up or redundant servers to prevent network downtime in the event of a failure of a particular server. In addition, although computer system 500 is depicted with various components, one skilled in the art will appreciate that the server can contain additional or different components. In addition, although aspects of an implementation consistent with the above are described as being stored in memory, one skilled in the art will appreciate that these aspects can also be stored on or read from other types of computer program products or computer-readable media, such as secondary storage devices, including hard disks, floppy disks, or CD-ROM; or other forms of RAM or ROM. The computer-readable media may include instructions for controlling a computer system, computer system 500, to perform a particular method, such as methods described above.

The contemplated modifications and variations specifically mentioned above are considered to be within the spirit and scope of the present invention.

Those of ordinary skill in the art will recognize that various modifications and variations may be made to the embodiments described above without departing from the spirit and scope of the present invention. It is therefore to be understood that the present invention is not limited to the particular embodiments disclosed above, but it is intended to cover such modifications and variations as defined by the following claims.

The invention claimed is:

1. A method for utilizing a biometric data brokerage system (BDPS) to transfer biometric records between at least one biometric collection device (BCD) and at least one biometric processing service (BPS), the method comprising:
   receiving, via a front-end BCD interface, biometric records in a first format transmitted by a first BCD, wherein the biometric records in the first format correspond to biometric data collected by the first BCD;
   translating, via an internal processes component, the biometric records in the first format received by the front-end BCD interface from the first format to a second format different from the first format; and
   transmitting, via a back-end BPS interface, the translated biometric records in the second format to a first BPS, wherein the translated biometric records in the second format is compatible with the first BPS;
   receiving, via the back-end BPS interface, a response from the first BPS in connection with the translated biometric records in the second format and a response from a second BPS in connection with translated additional biometric records in an additional format, wherein the additional format is different from the first format and the second format;
   combining, via the internal processes component, data corresponding to the response from the first BPS and data corresponding to the response from the second BPS to form a single report; and
   transmitting, via the front-end BCD interface, the single report to the first BCD.

2. The method of claim 1 further comprising:
   receiving, via the front-end BCD interface, biometric records in a third format transmitted by a second BCD, wherein the biometric records in the third format correspond to biometric data collected by the second BCD;
   translating, via the internal processes component, the biometric records in the third format received by the front-end BCD interface from the third format to a fourth format, wherein the third format is different from the first and second formats, and the fourth format is different from the first, second, and third formats; and
   transmitting, via the back-end BPS interface, the translated biometric records in the fourth format to a second BPS, wherein the translated biometric records in the fourth format is compatible with the second BPS.

3. The method of claim 1 wherein the receiving further comprises receiving, via the front-end BCD interface, the additional biometric records in a third format transmitted by the first BCD, and wherein the additional biometric records in the third format correspond to additional biometric data collected by the first BCD;
   wherein the translating further comprises translating, via the internal processes component, the additional biometric records in the third format received by the front-end BCD interface from the third format to the additional format, wherein the additional format is a fourth format, and wherein the third format is different from the first and second formats, and the fourth format is different from the first, second, and third formats; and wherein the transmitting further comprises transmitting, via the back-end BPS interface, the translated additional biometric records in the fourth format to a second BPS, and wherein the translated additional biometric records in the fourth format is compatible with the second BPS.

4. The method of claim 1 wherein the data corresponding to the response from the first BPS and the data corresponding to the response from the second BPS correspond to a single individual.

5. The method of claim 1 wherein the first BCD is not in direct contact with the first BPS.

6. The method of claim 1 further comprising managing, via a biometric interface module (BIM), security, credential management, and authentication to establish a connection with the first BPS.

7. A method for transferring biometric records between at least one biometric collection device (BCD) and at least one biometric processing service (BPS) comprising:
providing a first BCD for collecting biometric data;
transmitting, via the first BCD, biometric records in a first format corresponding to the biometric data collected by the first BCD;
receiving, via a biometric data brokerage system (BDPS), the biometric records in the first format transmitted by the first BCD;
translating, via the BDPS, the biometric records in the first format from the first format to a second format different from the first format;
transmitting, via the BDPS, the translated biometric records in the second format;
receiving, via a first BPS, the translated biometric records in the second format transmitted by the BDPS, wherein the translated biometric records in the second format is compatible with the first BPS;
receiving, via a back-end BPS interface, a response from the first BPS in connection with the translated biometric records in the second format and a response from a second BPS in connection with translated additional biometric records in an additional format, wherein the additional format is different from the first format and the second format;
combining, via the internal processes component, data corresponding to the response from the first BPS and data corresponding to the response from the second BPS to form a single report; and
transmitting, via the front-end BCD interface, the single report to the first BCD.

8. The method of claim 7 further comprising:
providing a second BCD for collecting biometric data;
transmitting, via the second BCD, biometric records in a third format corresponding to the biometric data collected by the second BCD;
receiving, via the BDPS, the biometric records in the third format transmitted by the second BCD;
translating, via the BDPS, the biometric records in the third format from the third format to a fourth format, wherein the third format is different from the first and second formats, and the fourth format is different from the first, second, and third formats;
transmitting, via the BDPS, the translated biometric records in the fourth format; and
receiving, via a second BPS, the translated biometric records in the fourth format transmitted by the BDPS, wherein the translated biometric records in the fourth format is compatible with the second BPS.

9. The method of claim 7 further comprising
transmitting, via the first BCD, additional biometric records in a third format corresponding to additional biometric data collected by the first BCD;
receiving, via the biometric data brokerage system (BDPS), the additional biometric records in the third format transmitted by the first BCD;
translating, via the BDPS, the additional biometric records from the third format to the additional format, wherein the additional format is a fourth format, wherein the third format is different from the first and second formats, and the fourth format is different from the first, second, and third formats;
transmitting, via the BDPS, the translated additional biometric records in the fourth format; and
receiving, via a second BPS, the translated additional biometric records in the fourth format transmitted by the BDPS, wherein the translated additional biometric records in the fourth format is compatible with the second BPS.

10. The method of claim 9 further comprising:
transmitting, via the first BPS, a second response in connection with the translated biometric records in the second format;
transmitting, via the second BPS, a second response in connection with the translated additional biometric records in the fourth format;
receiving, via the BDPS, the second response transmitted by the first BPS in connection with the translated biometric records in the second format and the second response transmitted by the second BPS in connection with the translated additional biometric records in the fourth format;
combining, via the BDPS, data corresponding to the second response transmitted by the first BPS and data corresponding to the second response transmitted by the second BPS to form a second single report; and
transmitting, via the BDPS, the single second report to the first BCD.

11. The method of claim 10 wherein the data corresponding to the second response transmitted by the first BPS and the data corresponding to the second response transmitted by the second BPS correspond to a single individual.

12. The method of claim 7 wherein the first BCD is not in direct contact with the first BPS.

13. The method of claim 7 further comprising managing, via a biometric interface module (BIM), security, credential management, and authentication to establish a connection with the first BPS.

14. A biometric data brokerage system (BDPS) for transfer of biometric records between at least one biometric collection device (BCD) and at least one biometric processing service (BPS), the BDPS comprising:
a memory configured to store computer executable instructions;
a processor configured to execute the computer executable instructions, the computer executable instructions comprising:
a front-end BCD interface that receives biometric records in a first format transmitted by a first BCD, wherein the biometric records in the first format correspond to biometric data collected by the first BCD;
an internal processes component that translates the biometric records in the first format received by the front-end BCD interface from the first format to a second format different from the first format; and a back-end BPS interface that transmits the translated biometric records in the second format to a first BPS, wherein the translated biometric records in the second format are compatible with the first BPS and the back-end BPS interface receives a response from the first BPS in connection with the translated biometric records in the second format and a response from a second BPS in connection with translated additional biometric records in an additional format, wherein the additional format is different from the first format and the second format;

wherein the internal processes component combines data corresponding to the response from the first BPS and data corresponding to the response from the second BPS to form a single report; and wherein the front-end BCD interface transmits the single report to the first BCD.

15. The BDPS of claim 14 wherein the front-end BCD interface receives biometric records in a third format transmitted by a second BCD, and wherein the biometric records in the third format correspond to biometric data collected by the second BCD;

wherein the internal processes component translates the biometric records in the third format received by the front-end BCD interface from the third format to a fourth format, and wherein the third format is different from the first and second formats, and the fourth format is different from the first, second, and third formats; and a back-end BPS interface that transmits the translated biometric records in the fourth format to a second BPS, wherein the translated biometric records in the fourth format is compatible with the second BPS.

16. The BDPS of claim 14 wherein the front-end BCD interface receives the additional biometric records in a third format transmitted by the first BCD, and wherein the additional biometric records in the third format correspond to additional biometric data collected by the first BCD;

wherein the internal processes component translates the additional biometric records in the third format received by the front-end BCD interface from the third format to the additional format, wherein the additional format is a fourth format, and wherein the third format is different from the first and second formats, and the fourth format is different from the first, second, and third formats; and wherein the back-end BPS interface transmits the translated additional biometric records in the fourth format to a second BPS, and wherein the translated additional biometric records in the fourth format is compatible with the second BPS.

17. The BDPS of claim 14 wherein the data corresponding to the response from the first BPS and the data corresponding to the response from the second BPS correspond to a single individual.

18. The BDPS of claim 14 wherein the first BCD is not in direct contact with the first BPS.

19. The BDPS of claim 14 further comprising a biometric interface module (BIM) that manages security, credential management, and authentication to establish a connection with the first BPS.

20. A system for transfer of biometric records between at least one biometric collection device (BCD) and at least one biometric processing service (BPS) comprising:

a first BCD that collects biometric data and transmits biometric records in a first format corresponding to the biometric data collected by the first BCD;

a biometric data brokerage system (BDPS) comprising:
  a front-end BCD interface that receives the biometric records in the first format transmitted by the first BCD;
  an internal processes component that translates the biometric records in the first format received by the front-end BCD interface from the first format to a second format different from the first format; and
  a back-end BPS interface that transmits the translated biometric records in the second format; and a first BPS that receives the translated biometric records in the second format transmitted by the back-end BPS interface, wherein the translated biometric records in the second format is compatible with the first BPS and the first BPS transmits a response in connection with the translated biometric records in the second format;

wherein a second BPS transmits a response in connection with the translated additional biometric records in an additional format, wherein the additional format is different from the first format and the second format;

wherein the back-end BPS interface receives the response transmitted by the first BPS in connection with the translated biometric records in the second format and a response transmitted by a second BPS in connection with translated additional biometric records in an additional format, wherein the additional format is different from the first format and the second format;

wherein the internal processes component combines data corresponding to the response transmitted by the first BPS and data corresponding to the response transmitted by the second BPS to form a single report; and wherein the front-end BCD interface transmits the single report to the first BCD.

21. The system of claim 20 further comprising:

a second BCD that collects biometric data and transmits biometric records in a third format corresponding to the biometric data collected by the second BCD, wherein the front-end BCD interface receives the biometric records in the third format transmitted by the second BCD, wherein the internal processes component translates the biometric records in the third format from the third format to a fourth format, wherein the third format is different from the first and second formats, and the fourth format is different from the first, second, and third formats, and wherein the back-end BPS interface transmits the translated biometric records in the fourth format; and a second BPS that receives the translated biometric records in the fourth format transmitted by the back-end BPS interface, wherein the translated biometric records in the fourth format is compatible with the second BPS.

22. The system of claim 20 further comprising a second BPS;

wherein the first BCD transmits additional biometric records in a third format corresponding to additional biometric data collected by the first BCD;

wherein the front-end BCD interface receives the additional biometric records in the third format transmitted by the first BCD;

wherein the internal processes component translates the additional biometric records from the third format to the additional format, wherein the additional format is a fourth format, and wherein the third format is different from the first and second formats, and the fourth format is different from the first, second, and third formats;

wherein the back-end BPS interface transmits the translated additional biometric records in the fourth format; and wherein the second BPS receives the translated additional biometric records in the fourth format transmitted by the back-end BPS interface, and wherein the translated additional biometric records in the fourth format is compatible with the second BPS.

23. The system of claim 20 wherein the data corresponding to the response transmitted by the first BPS and the data corresponding to the response transmitted by the second BPS correspond to a single individual.

24. The system of claim 20 wherein the first BCD is not in direct contact with the first BPS.

25. The system of claim 20 wherein the BDPS further comprises a biometric interface module (BIM) that manages security, credential management, and authentication to establish a connection with the first BPS.

* * * * *